US008270692B2

(12) United States Patent
Cotton et al.

(10) Patent No.: US 8,270,692 B2
(45) Date of Patent: Sep. 18, 2012

(54) METHODS AND APPARATUS FOR QUANTIFYING PHOTO-DAMAGE

(75) Inventors: Symon D. Cotton, Great Gransden (GB); Robert J. Morse, Cambridge (GB); Mark Chellingworth, Vale of Glamorgan (GB)

(73) Assignee: Medx Health Corporation, Mississauga, Ontario (CA)

( * ) Notice: Subject to any disclaimer, the term of this patent is extended or adjusted under 35 U.S.C. 154(b) by 879 days.

(21) Appl. No.: 12/212,989

(22) Filed: Sep. 18, 2008

(65) Prior Publication Data

US 2009/0080727 A1 Mar. 26, 2009

(30) Foreign Application Priority Data

Sep. 26, 2007 (EP) .................................... 07253823

(51) Int. Cl.
*G06K 9/00* (2006.01)
(52) U.S. Cl. .......................................................... 382/128
(58) Field of Classification Search ........................ None
See application file for complete search history.

(56) References Cited

U.S. PATENT DOCUMENTS

| 5,016,173 | A | * | 5/1991 | Kenet et al. ................... 382/128 |
| 5,836,872 | A | | 11/1998 | Kenet et al. |
| 7,916,910 | B2 | * | 3/2011 | Cotton et al. ................... 382/128 |
| 2005/0197542 | A1 | | 9/2005 | Bazin et al. |
| 2006/0142662 | A1 | * | 6/2006 | Van Beek ....................... 600/476 |
| 2006/0239547 | A1 | * | 10/2006 | Robinson et al. .............. 382/118 |
| 2008/0056995 | A1 | * | 3/2008 | Timmins ........................ 424/9.2 |
| 2008/0107320 | A1 | * | 5/2008 | Cotton ........................... 382/131 |
| 2008/0319283 | A1 | * | 12/2008 | Cotton et al. .................. 600/306 |
| 2009/0043363 | A1 | * | 2/2009 | Cotton et al. .................... 607/88 |
| 2009/0080726 | A1 | * | 3/2009 | Cotton et al. .................. 382/128 |

FOREIGN PATENT DOCUMENTS

| GB | 2429385 | 2/2007 |
| WO | WO 2004111621 | 12/2004 |
| WO | WO 2006127190 | 11/2006 |

OTHER PUBLICATIONS

European Search Report for corresponding priority application, Mar. 11, 2008, 3 pages.

* cited by examiner

*Primary Examiner* — Jermele M Hollington
(74) *Attorney, Agent, or Firm* — Tracy Jong Law Firm; Tracy P. Jong

(57) ABSTRACT

A method of obtaining a measurement of the extent of telangectasia in an area of skin is disclosed. Initially (S3-1) an image of an area of skin (2) to be analyzed is obtained. The obtained image is then processed (S3-2-S3-3) to determine blood distribution data indicative of the distribution of blood in an imaged area of skin. This blood distribution data is then converted (S3-5) using a Discrete Fourier Transform and the converted blood distribution data is then processed to obtain a measurement of the extent features in a determined distribution of blood correspond to structures of a predetermined size. The obtained measurement of the extent of telangectasia can then be combined (s3-6) with other measurements of the effects of photo-damage such as measurements of melanin disorder and collagen degradation to obtain a measurement of the extent of photo-damage.

21 Claims, 3 Drawing Sheets

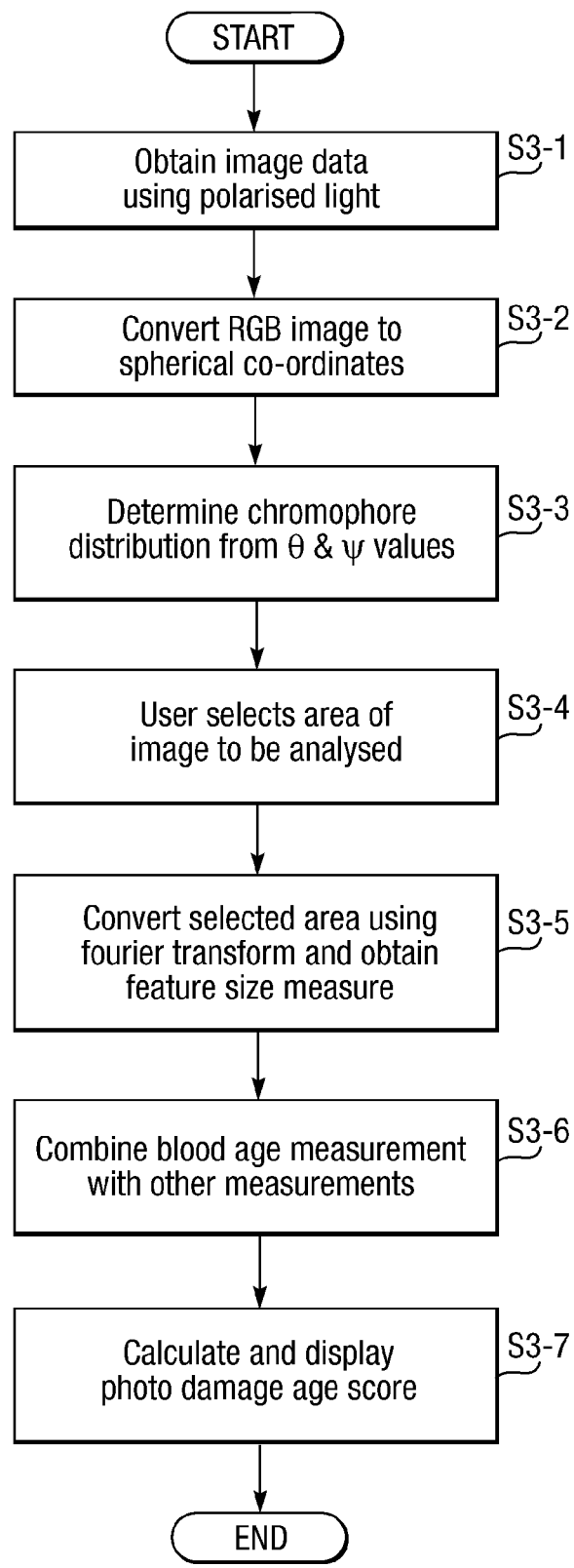

METHODS AND APPARATUS FOR QUANTIFYING PHOTO-DAMAGE

TECHNICAL FIELD

The present application concerns methods and apparatus for quantifying photo-damage.

BACKGROUND

Much of the change of the appearance of skin due to aging such as age spots (irregularities in melanin distribution), telangectasia (abnormal, small blood vessels) and collagen degradation (characterized by yellow-brown discolouration) primarily arises from photo-damage caused by chronic sun exposure.

Original research undertaken at the University of Birmingham, subsequently described in WO 98/122023 argued that the Kubelka-Munk theory is sufficient to model light transport within skin. If exact scattering and absorption coefficients can be specified, then the Kubelka-Munk theory can be applied at each wavelength in the visible range and corresponding remittance spectrum obtained. This predicted spectrum, which will determine the colour of the skin, will be dependent on the histological characteristics of the tissue. Three parameters capture most of the variation in remitted spectra from healthy skin. These three parameters are concentration of epidermal melanin, concentration of blood and thickness of the papillary dermal layer (collagen thickness).

Using the RGB response curves for a digital camera together with a model of the scattering and absorption characteristics of the skin, it is possible to calculate the set of image values which would be measured by a digital camera when skin with a known remittance spectrum $S(\lambda)$ is illuminated with light of known spectral characteristics $I(\lambda)$. This is done by calculating the convolution integral for each channel, given as, $$i_{red} = \int I(\lambda)S(\lambda)R(\lambda)d\lambda, \; i_{green} = \int I(\lambda)S(\lambda)G(\lambda)d\lambda, \; i_{blue} = \int I(\lambda)S(\lambda)B(\lambda)d\lambda$$

where $R(\lambda)$, $G(\lambda)$ and $B(\lambda)$ are the response curves for the red, green and blue channels and $i_{red}$, $i_{blue}$ and $i_{green}$ are the corresponding values recorded by the camera at a given pixel.

By ranging through all potential combinations of melanin, blood and collagen, it is possible to generate all possible spectra and therefore all possible sets of image values which would be measured by a digital camera. Once this information has been obtained a link can be established between image values and histological parameter values. This link can be expressed as a mathematical function.

Determining measurements of epidermal melanin, blood, collagen and dermal melanin directly from measurements of remitted light $S(\lambda)$ requires that an area of skin is illuminated with light of known spectral characteristics. However, as is discussed in detail in Astron Clinica's prior patent application WO 04/010862 determining measurements from ratios of image values enables measurements of blood and melanin concentration to be obtained without the need for strict lighting control and calibration.

Although obtaining measurements of blood and melanin concentrations provide a further means for classifying the appearance of skin, obtaining a reliable measure of the extent of photo-damage remains difficult as photo-damage causes a variety of different histological and physiological changes. Although clinical scoring systems exist, such existing scoring systems all require subjective user interpretation of pigmentary irregularities.

BRIEF DESCRIPTION OF THE DRAWINGS

FIG. 3 is a flow diagram of the processing performed by the photo damage measurement system of FIG. 2.

DETAILED DESCRIPTION OF THE DISCLOSURE

Interaction of Light with the Skin

By way of background and to assist understanding, before describing embodiments of the present invention, the physical structure of skin and the interaction of skin with light will first be briefly explained with reference to FIG. 1.

Figure 1:
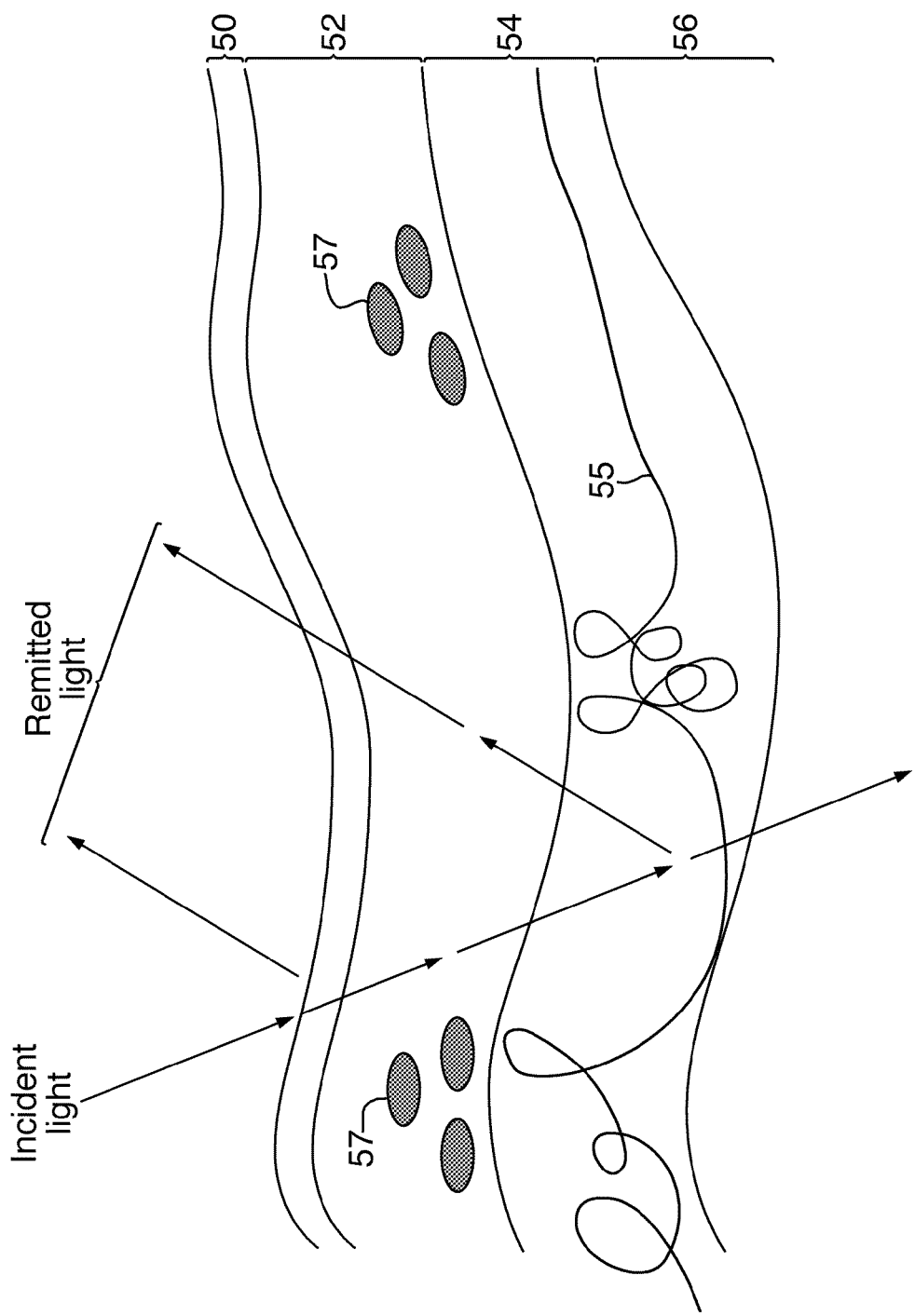
FIG. 1 is a schematic cross sectional view through a layer of skin illustrating the structure of the skin and the interaction of that structure with incident light.

As shown in FIG. 1, skin has a layered structure comprising an outer cornified layer 50 also known as the stratum corneum, the epidermis 52, and the dermis which itself can be divided into the papillary dermis 54 which contains the blood supply 55 for the skin and the reticular dermis 56.

When light is incident on the skin, much of the light is immediately reflected when coming into contact with the outer cornified layer 50. A proportion of incident light does, however, pass through the cornified layer 50 and proceeds to interact with the constituents of the epidermis 52 and the papillary dermis 54. As light passes through the epidermis 52 and the papillary dermis 54 the light is absorbed by various chromophores present in the skin, most notably chromophores such as haemoglobin present in the blood in blood vessels 55 in the papillary dermis, melanin, a pigment produced by melanocytes 57 in the epidermis 52 and collagen a fibrous material present throughout the skin. By the time the incident light reaches the reticular dermis 56 the scattering of light is highly forward and therefore for that reason the reticular dermis 56 can for all intents and purposes be considered returning no light.

In addition to chromophores present in the epidermis 52 and papillary dermis 54 absorbing various wavelengths, certain structures in the skin most notably collagen cause incident light to be reflected The interaction of light with collagen in the skin is such to cause the light to loose any original polarization. The outward appearance of the skin can therefore be considered to be a mixture of the light immediately reflected by the cornified layer 50 and the remitted light which has interacted with the chromophores present in the epidermis 52 and the papillary dermis 54.

As will be described the present invention utilises the fact that the appearance of the skin is dependent upon the reflection of light from the surface of the skin and the interaction of light with structures and chromophores below the surface to obtain a measurement of photo damage.

Specific Embodiment

Figure 2:
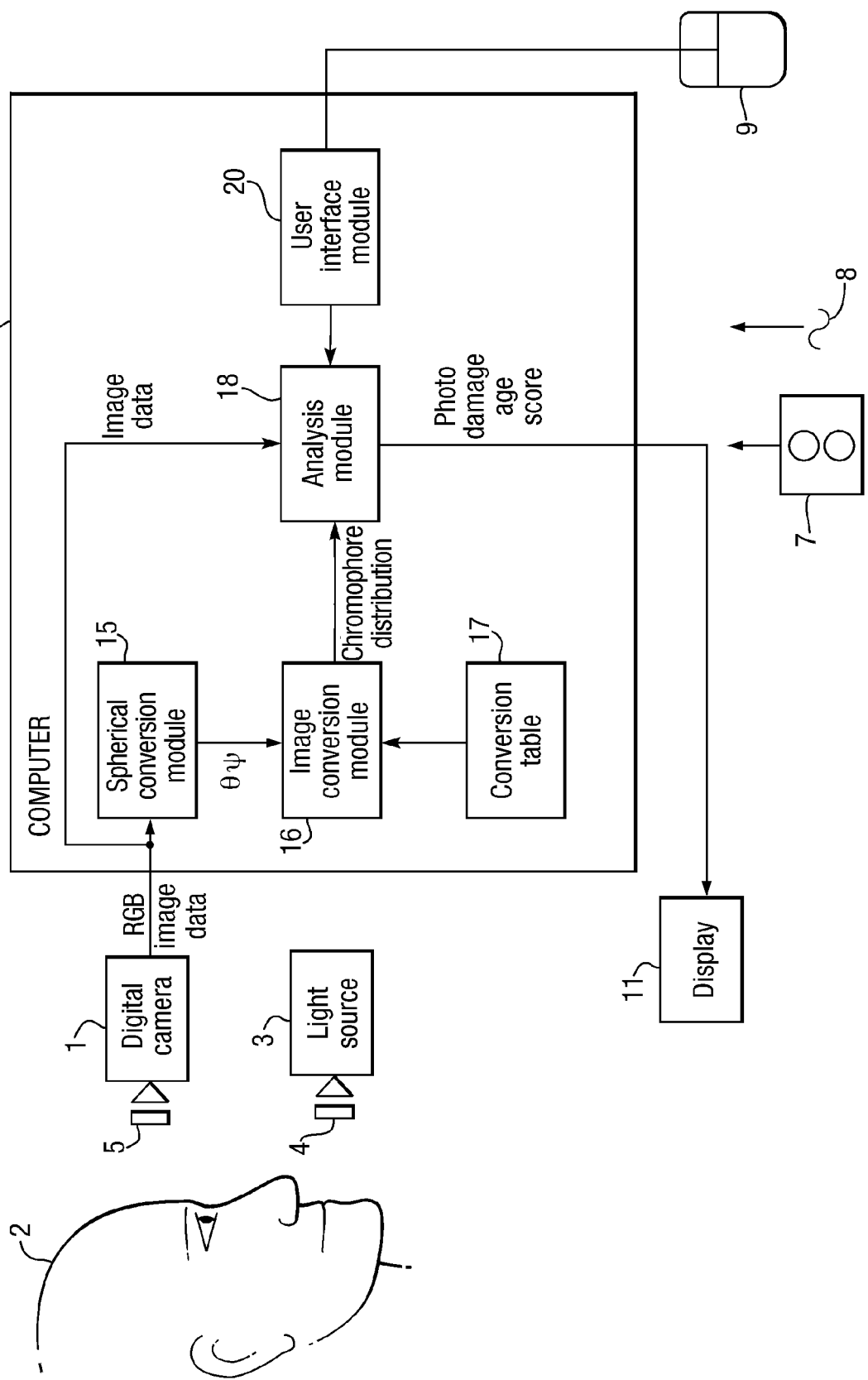
FIG. 2 is a schematic block diagram of a photo damage measurement system in accordance with a second embodiment of the present invention.

Referring to FIG. 2 which is a schematic block diagram of an embodiment of the present invention, a photo damage measurement system is provided which comprises a conventional digital camera 1 which is arranged to obtain an image of an individual 2 illuminated by a light source 3.

A first polarizer 4 is then provided at a position in front of the light source 3 which causes the light source 3 to illuminate an individual 2 with polarized light. A second polarizer 5 is then provided in front of the lens of digital camera 5 with the two polarizers 4,5 being arranged so that the second polarizer 5 filters light polarized by the first polarizer 4.

The digital camera 1 is arranged to obtain images of an individual 2 illuminated by the light source 3 and then pass these images to a computer 6 which is configured by software either provided on a disk 7 or by receiving an electrical signal 8 via a communications network to be configured into a number of functional modules 15-20. Also connected to the computer 6 is a mouse 9. The functional modules 15-20 process image data received from the camera I on the basis of user input via the mouse 9 to determine a photo-damage measure for a selected area of skin. The photo-damage measure is then shown on the display 10 together with illustrations of the individual's skin and indications of concentrations of chromophores appearing in the individual's skin.

In the present embodiment the functional modules comprise: a spherical conversion unit 15 for converting RGB image data into corresponding spherical co-ordinates; an image conversion module 16 and a conversion table 17 for processing spherical angular co-ordinates to generate data indicative of concentrations of blood and melanin, which hereinafter will be referred to as the blood image and the melanin image respectively; an analysis module 18 operable to calculate a photo damage age score for a user selected area of skin; and a user interface module 20 which interprets user input via the mouse 9 such that a user can select an imaged area of skin for processing.

Processing of Obtained Image Data

Referring to FIG. 3 which is a flow diagram of the processing performed by the computer 6 of FIG. 2, initially (S3-1) an image is obtained by the digital camera 1 of the individual 2 illuminated by the light source 3 with the first polarizer 4 positioned so that the individual 2 is illuminated by polarized light. The presence of the second polarizer 5 will then mean that the image obtained by the camera 1 will be dependent upon the interaction of the light with the underlying structures of the skin being imaged since any light reflected directly from the surface of the skin will be filtered by the second polarizer 5.

In this embodiment as the digital camera 1 comprises a conventional digital camera, the image data generated by the digital camera 1 comprises RGB values ranging from 0 to 255 for a large array of pixels where the RGB values are indicative of the extent light received by a photo receptor within the camera 1 for each pixel in an image appears to be red, green and blue where a completely black pixel has RGB values of 0, 0, 0 and a completely bright white pixel has RGB values of 255, 255, 255.

When an image of an individual 2 illuminated by polarized light has been obtained by the camera 12, the image is processed (s3-2; s3-3) to derive chromophore data indicative of the concentrations of blood and melanin, the blood image and melanin image respectively, in the area of the skin being analysed. This blood image data and melanin image data together with the original image data is then passed to the analysis module 18 for processing to obtain a measurement of photo damage which will be described later.

Determination of Blood and Melanin Concentrations

The determination of concentrations of blood and melanin is achieved by passing the obtained image to the spherical conversion module 15 which converts (S3-2) the conventional RGB data for each pixel in an image into a corresponding set of spherical co-ordinates θ ψ r where the spherical angles of θ ψ are substantially indicative of the hue and chromaticity represented by an individual pixel in an image captured by the digital camera 1 and the radial co-ordinate r is substantially indicative of the brightness of the pixel.

This conversion is achieved in a conventional manner with $$\theta = \cos^{-1}(B(R^2+B^2+G^2)^{-1/2})$$

$$\psi = \tan^{-1}(G/R)$$

and $r = (R^2+B^2+G^2)^{1/2}$

The conversion is performed for each pixel in the original pixel array for the image generated by the digital camera. The result of the conversion is a set of spherical θ ψ r co-ordinates for each pixel in the original image.

Arrays of the calculated angular spherical co-ordinates θ and ψ are in this embodiment passed to the image conversion module 16.

After the spherical conversion module 15 has converted the RGB values for an image into spherical co-ordinates, the image conversion module 16 then processes (s3-3) the generated array of θ and ψ values to obtain values indicative of the concentration of blood and melanin at individual points on the surface of the skin of the individual.

In this embodiment this is achieved by processing each pair of θ and ψ values for each pixel in an array in turn by scaling the θ and ψ values so that instead of comprising values between π and −π, and 0 and π/2, the scaled θ and ψ values comprise integer values ranging between 0 and 255. These scaled θ and ψ values are then utilised to access the conversion table 17 which in this embodiment is a 255 by 255 a lookup table associating pairs of scaled θ and ψ co-ordinates with pairs of concentrations of blood and melanin liable to give rise to such scaled θ and ψ values. In this embodiment, the conversion table 17 comprises a table associating blood and melanin concentrations with various θ and ψ values, where the θ and ψ values fall within the expected range of the colour space for skin. In the event that the combination of θ and ψ values for a particular pixel falls outside the range of values for which chromophores concentration data is stored within the conversion table 17, in this embodiment the conversion module 16 returns a null value for the concentration of blood and melanin for the pixel with θ and ψ values for the pixel.

After chromophore distribution values for blood and melanin for each of the pixels in an image have been calculated by the conversion module 16, the resulting blood and melanin images are then passed by the conversion module 16 to the analysis module 18. When the chromophore distribution values are received by the analysis module 18, the analysis module 18 then calculates a photo damage score from the three received images as will now be described.

Calculation of Skin Photo Damage Score

The degree of photo damage to an individual's skin is strongly correlated with the individual's age, due to correlation of age with degree of chronic sun exposure. The photo damage itself can however result in a variety of different symptoms such as age spots, telangectasia and collagen degradation. A measurement of photo-damage can therefore be achieved by obtaining a measurement of the extent of any of these symptoms. Further, as each symptom has a different physiological cause, the extent of each symptom is not necessarily cross correlated with one another. An improved overall photo-damage measure can therefore be obtained by considering the extent of the various different effects of chronic photo-exposure.

(i) Determining a Measurement of Telangectasia

In the case of telangectasia (the presence of larger visible blood vessels in the skin) a measurement of the extent of telangectasia can be obtained by processing a blood image to determine a count of the numbers of apparent blood vessels of a certain size. The calculation of such a measurement will now be described.

When the chromophore distribution values are received, the analysis module 18 prompts the user to select (s3-4) an area of skin of the individual 2 to be analysed by displaying the obtained image of skin on the display 10. The user then can proceed to identify an area of skin for detailed analysis by controlling a pointer using the mouse 9. The selected area, e.g. the cheek, should be substantially uniform in surface geometry and have few features or obvious lesions. In this embodiment, in response to user selection the analysis module 18 selects a square of 256 by 256 pixels for further processing centred on the position identified by the location of the pointer on the display 10.

The analysis module 18 then processes (s3-5) the selected 256 by 256 pixels square from the blood image by converting the square using a conventional Fast Fourier Transform (FFT) such as, for example, the Fast Fourier Transform (FFT) function in Matlab.

The result of this FFT operation performed by the analysis module 18 is to produce a complex coefficient corresponding to each of the pixels in the 256 by 256 pixels square from the blood image. The imaginary part of this complex coefficient is discarded and the real part of this coefficient is stored in a 256 by 256 array.

Processing the image in this way enables a measurement of the relative numbers of blood vessels of a certain size to be obtained. This is because the values of the real coefficients stored in the array are indicative of the number of features of a particular size present in the sampled area of the blood image, where the relative location of a coefficient within the array is indicative of the feature's size and orientation.

More specifically, the coefficient at the centre of the 256 by 256 array of real numbers produced by the FFT corresponds to a count of large objects in the selected 256 by 256 pixels square of the blood image. The relative size of features represented by the other coefficients then decreases with distance from this centre position with the orientation of features being indicated by its relative position amongst the coefficients at a particular distance from the centre. The number of features of a particular size in the 256 by 256 pixels square of the blood image can therefore be calculated from the average value of real numbers at a distance from the centre of the 256 by 256 array which corresponds to the particular size of the feature.

Although, the apparent size of blood vessel associated with telangectasia will depend upon the distance between the camera 1 and the skin 2 being imaged, and the size of pixels for images generated by the camera 1, the applicants have discovered through empirical results that taking an average value of coefficients corresponding to the expected size of blood vessels associated with telangectasia is robust for a reasonable variation in size. This is because the result of this average measure for any particular selected size is merely a measure of the presence of visible blood vessels of corresponding to that particular size and telangectasia will be represented by the presence abnormal blood vessels across a range of sizes.

Thus in this embodiment, a measurement of the extent of telangectasia is therefore obtained by taking an average value for all of the real coefficients representing features of one of size corresponding to blood vessels effected by telangectasia. This is achieved by averaging the coefficient values of all the coefficients a set distance from the centre of the array of real coefficients where the distance of a point in the array corresponds to a Euclidian distance determined by the relative x,y co-ordinates associated with a coefficient relative to co-ordinates for the centre of the array. Thus in this way a measure of the number of features in the blood image corresponding to blood vessels effected by telangectasia is obtained which is independent of the orientation of those features.

In addition to the telangectasia measurement described above, another physiological characteristic indicative of photo damage that is apparent in the blood image is the depth of colour of the blood vessel. That is, the degree of telangectasia may also be seen from the extent of blood concentration in the abnormal blood vessels as well as the number of abnormal blood vessels themselves. This characteristic can be found from the blood image by identifying the pixel with the coefficient of greatest magnitude.

This Blood Maximum score is largely independent of the telangectasia score derived from the number of abnormal blood vessels of a certain size and therefore an improved measurement of telangectasia can be obtained by calculating a weighted average of the two measurements. An alternative to identifying the blood maximum would be to determine the average concentration of blood as apparent in the blood image. This is because variation in average blood concentration in a sample of skin is well correlated with the blood maximum concentration value.

When a telangectasia score has been obtained as described above, this is combined (s3-6) with a number of other measurements including measurements relating to age spots and collagen degradation.

(ii) Determining a Measurement of the Extent of Age Spots

Unlike telangectasia, age spots are characterised by irregularity in the distribution of melanin rather than the size of any particular feature in the melanin image. Any suitable method of measuring the irregularity in melanin distribution can therefore be used to obtain a measurement of the extent of the development of age spots.

One suitable method would be to process the obtained melanin image to obtain a conventional mathematical measure of the entropy of the melanin image such as the entropy function in Matlab.

Alternatively, the FFT method as described above in relation to the blood image could be used to obtain a measurement of the number of small sized features in the melanin image by taking an average value of real numbers at the perimeter of the 256 by 256 array produced by the FFT, which relates to high frequency variation in the melanin image.

(iii) Determining a Measurement of the Extent of Collagen Degradation

Collagen degradation such as is caused by solar elastosis is characterised by a sallowness of skin giving a yellow-brown discolouration. To measure collagen degradation, therefore, it is the hue of the image rather than the intensity which is relevant. A measurement of collagen degradation of the skin can therefore be determined by calculating the number of pixels in the original image obtained by the camera 1 which are of a hue corresponding to the distinctive colour arising due to collagen degradation as a fraction of the total number of pixels in the original image.

(iv) Determining an Overall Measurement of Skin Photo-Damage

As indicated above the extent of skin photo-damage is largely correlated with age. A useful measurement of photo-damage can therefore be obtained by converting the individual measurements of the various symptoms of photo-damage into a single score which is indicative of the apparent age of the sample of imaged skin. This photo damage age score can be achieved by determining a final weighted average of the symptom scores described above, wherein the measurements are weighted in such a way so as to best correlate with age. Suitable weightings for the various measurements can be determined by performing multivariate linear regression between the obtained symptom measurements and the ages of a suitable sample population.

Thus for example one suitable equation for converting symptom scores into an overall age score based on a sample of images of women with Caucasian skin types has been found to be:

Predicted skin age=5.249*melanin entropy−36*melanin high frequency Fourier measurement+ 37.797*telangectasia Fourier measurement+ 0.007*Blood Max measurement−125.608, where melanin entropy, melanin high frequency Fourier measurement, telangectasia Fourier measurement and Blood Max measurement are measurements as described above.

Another suitable equation for converting symptom scores into an overall age score based on a sample of images of men with Caucasian skin types has been found to be:

Predicted skin age=29.685*telangectasia Fourier measurement−33.931*Fraction 1−10628.139 Fraction 2−55.543 where telangectasia Fourier measurement is a measurement as described above and Fraction1 and Fraction 2 are two measurements of the fraction of pixels of an image having hues corresponding to hues associated with collagen degradation.

It will be appreciated that other suitable measurements combining a number of symptom measurements could be determined using different population samples.

After combining (s3-6) the respective measurements, the analysis module 18 calculates and displays (s3-7) the photo damage age score.

Modifications and Alternatives

In the above described embodiment, blood and melanin images are described as being determined the processing of image data from the original image from the camera 1, by converting an original image to spherical co-ordinates and determining chromophore distribution from these spherical co-ordinates. It will be appreciated that the invention is not limited to these specific details and that any suitable method of deriving blood and melanin images could be used. Thus for example measurements of blood and melanin could be determined based on measurements of remitted light alone or alternatively based on measurements of ratios of remitted spectra. More generally any suitable means for obtaining a measurement or an approximation of a measurement of blood and/or melanin concentrations could be utilised In the above embodiment, two equations for calculating the photo damage age score have been given, where the equations comprise specific weighting values obtained using linear regression. The two specific equations correspond to two specific databases of images which each contain images of specific skin types. It will be appreciated that the present invention is not limited to specific databases or specific skin types. Rather it will be appreciated that linear regression may be used to derive an equation to convert the symptom scores into a photo damage age score for individuals of any age, gender or skin type utilising linear regression of measurements from an appropriate database of skin samples It will also be appreciated that rather than storing only a single means for combining measurements of photo-damage related symptoms into a skin photo damage score, multiple equations could be stored. In such a system, a user could be prompted to input a skin type or alternatively a skin type might be detected by processing an image and then an appropriate equation for obtaining a skin photo damage score for the identified skin type could be selected and used.

Further, although in the above embodiment, a system has been described in which a single skin photo damage score is generated and output, it will be appreciated that generated scores could be utilised in different ways. Thus for example, instead of outputting a skin photo damage score which a user could compare with their chronological age, a user could be requested to input their chronological age and the difference between their actual age and the age identified by a generated skin photo damage score could be displayed. In alternative embodiments, instead of outputting a skin photo-damage score data could be pre-stored indicating the range of scores associated with individuals of an specific age and an indication of the relative score for an individual relative to the range of scores for individuals of a specific age could be output.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance oft the relevant processes.

The invention claimed is:

1. A method of obtaining a measurement of the extent of telangectasia in an area of skin comprising:
   receiving an image of an area of skin to be analyzed;
   processing the obtained image to determine blood distribution data indicative of the distribution of blood in an imaged area of skin;
   converting the determined blood distribution data to a frequency domain representation of the blood distribution data; and
   processing the converted blood distribution data to obtain a measurement of the number of features of a predetermined size in the determined distribution of blood; and
   using the measurement of number of features of a predetermined size to obtain a measurement of the extent of telangectasia in the area of skin.

2. The method of claim 1, wherein processing the converted blood distribution data to obtain a measurement of the number of features of a predetermined size comprises:
   identifying from an array of real coefficients generated by converting blood distribution data using a Discrete Fourier Transform, coefficients corresponding to features of a predetermined size; and
   calculating an average value of said identified real coefficients.

3. The method of claim 1 further comprising:
   identifying a maximum blood concentration using the obtained blood distribution data;

obtaining a measurement of the extent of telangectasia using the maximum blood concentration; and determining a weighted average of the measurement of the extent of telangectasia obtained using the determined maximum blood concentration and said measurement of the extent of telangectasia obtained from the number of features of a predetermined size.

4. The method of claim 1 further comprising:

identifying an average blood concentration using the obtained blood distribution data;

obtaining a measurement of the extent of telangestasia using the average blood concentration; and determining a weighted average of the measurement of the extent of telangectasia obtained using the determined average blood concentration and said measurement of the extent of telangestasia obtained from the number of features of a predetermined size.

5. A method of obtaining a measurement of the extent of photo damage in an area of skin comprising:

obtaining a measurement of the extent of telangectasia in accordance with the method of claim 1;

processing the obtained image to determine melanin distribution data indicative of the distribution of melanin in an imaged area of skin;

determining a measurement of the extent of disorder in the distribution of melanin in the imaged area of skin; and determining a weighted average of the determined measurement of the extent of telangectasia and said determined measurement of the extent of disorder in the distribution of melanin in the imaged area of skin to provide a measurement of the extent of photo damage in the area of skin.

6. A method of obtaining a measurement of the extent of photo damage in an area of skin comprising:

obtaining a measurement of the extent of telangectasia in accordance with the method of claim 1;

processing the obtained image to identify the proportion of an image having a hue corresponding to a hue associated with the appearance of degraded collagen; and determining a weighted average of the determined measurement of extent of telangectasia and said identified proportion of an image having a hue corresponding to a hue associated with the appearance of degraded collagen to provide a measurement of the extent of photo damage in the area of skin.

7. The method of claim 3, further comprising:

selecting weights for determining weighted averages of measurements, wherein said weights are selected so as to best correlate with age.

8. The method of claim 7 wherein said sampled population comprises a sampled population sharing at least one of gender and skin type.

9. A computer readable medium storing computer interpretable instructions which when interpreted by a programmable computer cause the computer to obtain an image of an area of skin to be analyzed;

process the obtained image to determine blood distribution data indicative of the distribution of blood in an imaged area of skin;

convert the determined blood distribution data to a frequency domain representation of the blood distribution data; and process the converted blood distribution data to obtain a measurement of the number of features of a predetermined size in the determined distribution of blood; and use the measurement of number of features of a predetermined size to obtain a measurement of the extent of telangectasia in the area of skin.

10. An apparatus for obtaining a measurement of the extent of photo-damage in an area of skin comprising:

a light source operable to illuminate an area of skin with polarized light;

a camera operable to obtain an image of remitted light of a different polarity to that with which the light source is operable to illuminate an area of skin remitted from an area of skin illuminated by the light source; and a processor configured to:

process an image obtained by the camera to determine blood distribution data indicative of the distribution of blood in the area of imaged skin;

convert the determined blood distribution data to a frequency domain representation of the blood distribution data; and process converted blood distribution data to obtain a measurement of the number of features of a predetermined size in the determined distribution of blood; and use the measurement of number of features of a predetermined size to obtain a measurement of the extent of telangectasia in the area of skin.

11. The apparatus of claim 10, wherein the processor is operable to process converted blood distribution data to obtain a measurement of the number of features of a predetermined size by:

identifying from an array of real coefficients generated by converting blood distribution data using a Discrete Fourier Transform, coefficients corresponding to features of a predetermined size; and calculating an average value of said identified real coefficients.

12. The apparatus of claim 10 wherein the processor is further operable to:

identify a maximum blood concentration using the obtained blood distribution data;

obtain a measurement of the extent of telangectasia using the maximum blood concentration; and determine a weighted average of the measurement of the extent of telangectasia obtained using the determined maximum blood concentration and said measurement of the extent of telangectasia obtained from the number of features of a predetermined size.

13. The apparatus of claim 10 wherein the processor is further operable to:

identify an average blood concentration using the obtained blood distribution data;

obtain a measurement of the extent of telangectasia using the average blood concentration; and determine a weighted average of the measurement of the extent of telangectasia obtained using the determined average blood concentration and said measurement of the extent of telangectasia obtained from the number of features of a predetermined size.

14. The apparatus of claim 10 wherein the processor is further operable to determine a measurement of the extent of photo-damage in an area of skin by:

processing an obtained image to determine melanin distribution data indicative of the distribution of melanin in an imaged area of skin;

determining a measurement of the extent of disorder in the distribution of melanin in the imaged area of skin; and determining a weighted average of a determined measurement of the extent of telangectasia and a determined measurement of the extent of disorder in the distribution of melanin in the imaged area of skin to provide a measurement of the extent of photo damage in the area of skin.

15. The apparatus of claim 10 wherein the processor is further operable to determine a measurement of the extent of photo-damage in an area of skin by:
   processing an obtained image to identify the proportion of an image having a hue corresponding to a hue associated with the appearance of degraded collagen; and
   determining a weighted average of the determined measurement of extent of telangectasia and said identified proportion of an image having a hue corresponding to a hue associated with the appearance of degraded collagen to provide a measurement of the extent of photo damage in the area of skin.

16. The apparatus of claim 12 wherein the processor is further operable to select weights for determining weighted averages of measurements, wherein said weights are selected so as to best correlate with age.

17. The apparatus of claim 16 wherein said sampled population comprises a sampled population sharing at least one of gender and skin type.

18. The method of claim 5 comprising:
   processing the obtained image to identify the proportion of an image having a hue corresponding to a hue associated with the appearance of degraded collagen;
   wherein said identified proportion is included in the determination of a weighted average.

19. The method of claim 18 in which the weighting factors are determined by performing multivariate linear regression between the measurements to be weighted and the ages of a sample population.

20. The apparatus of claim 14 wherein the processor is further operable to:
   process the obtained image to identify the proportion of an image having a hue corresponding to a hue associated with the appearance of degraded collagen;
   wherein said identified proportion is included in the determination of a weighted average.

21. The apparatus of claim 20 in which the processor is configured to determine the weighting factors by performing multivariate linear regression between the measurements to be weighted and the ages of a sample population.

* * * * *